(12) United States Patent
Neumann

(10) Patent No.: US 11,684,316 B2
(45) Date of Patent: Jun. 27, 2023

(54) ARTIFICIAL INTELLIGENCE SYSTEMS AND METHODS FOR GENERATING LAND RESPONSES FROM BIOLOGICAL EXTRACTIONS

(71) Applicant: KPN Innovations, LLC, Lakewood, CO (US)

(72) Inventor: Kenneth Neumann, Lakewood, CO (US)

(73) Assignee: KPN INNOVATIONS, LLC., Lakewood, CO (US)

( * ) Notice: Subject to any disclaimer, the term of this patent is extended or adjusted under 35 U.S.C. 154(b) by 573 days.

(21) Appl. No.: 16/825,200

(22) Filed: Mar. 20, 2020

(65) Prior Publication Data

US 2021/0290174 A1    Sep. 23, 2021

(51) Int. Cl.
| | |
|---|---|
| *A61B 5/00* | (2006.01) |
| *G06N 20/00* | (2019.01) |
| *G06Q 50/16* | (2012.01) |
| *H04W 4/029* | (2018.01) |
| *H04W 4/021* | (2018.01) |
| *G06N 5/04* | (2023.01) |
| *G06Q 30/0601* | (2023.01) |

(52) U.S. Cl.
CPC ............ *A61B 5/7264* (2013.01); *G06N 5/04* (2013.01); *G06N 20/00* (2019.01); *G06Q 30/0631* (2013.01); *G06Q 50/16* (2013.01); *G06Q 50/165* (2013.01); *H04W 4/021* (2013.01); *H04W 4/029* (2018.02)

(58) Field of Classification Search
None
See application file for complete search history.

(56) References Cited

U.S. PATENT DOCUMENTS

| | | |
|---|---|---|
| 5,361,201 A | 11/1994 | Jost et al. |
| 10,255,550 B1 | 4/2019 | Simkoff et al. |
| 10,536,294 B2 | 1/2020 | Wang |

(Continued)

OTHER PUBLICATIONS

Lacuesta, etl,al, System to Recommend the Best Place to Live Based on Wellness State of the User Employing the Heart Rate Variability, May 10, 2017, Digital Object Identifier 10.1109/ACCESS.2017.2702107, 10594-10604.*

(Continued)

*Primary Examiner* — Peter Ludwig
*Assistant Examiner* — Donald J Edmonds
(74) *Attorney, Agent, or Firm* — Caldwell Intellectual Property Law

(57) ABSTRACT

An artificial intelligence system for generating land responses from biological extractions. The artificial intelligence system includes a computing device, configured to retrieve, a biological extraction pertaining to a user, wherein the biological extraction contains at least an element of physiological data. The computing device is configured to locate, a land descriptor wherein the land descriptor identifies a property. The computing device is configured to generate, a land machine-learning model, wherein the land machine-learning model utilizes the biological extraction as an input and outputs property elements. The computing device is configured to determine the suitability of the property utilizing the output property elements.

18 Claims, 5 Drawing Sheets

(56) References Cited

U.S. PATENT DOCUMENTS

| | | | |
|---|---|---|---|
| 2012/0084092 A1* | 4/2012 | Kozuch | G16H 10/20 |
| | | | 705/2 |
| 2014/0379365 A1* | 12/2014 | De Roode | G16H 10/20 |
| | | | 705/2 |
| 2015/0242747 A1 | 8/2015 | Packes et al. | |
| 2016/0239624 A1* | 8/2016 | Short | A61B 3/113 |
| 2017/0236226 A1 | 8/2017 | Malaviya et al. | |
| 2018/0068329 A1 | 3/2018 | Ganti et al. | |
| 2018/0082317 A1* | 3/2018 | Reier | G16H 70/20 |
| 2018/0174669 A1* | 6/2018 | Lazaryev | G16H 70/20 |
| 2018/0181591 A1 | 6/2018 | Bryant | |
| 2018/0253780 A1* | 9/2018 | Wang | H04L 51/02 |
| 2018/0374171 A1 | 12/2018 | Aizen et al. | |
| 2019/0043144 A1 | 2/2019 | Hildebrand | |
| 2019/0065690 A1* | 2/2019 | Wu | G16H 80/00 |
| 2019/0080425 A1 | 3/2019 | Bui et al. | |
| 2019/0130505 A1 | 5/2019 | Hiltch et al. | |
| 2019/0209022 A1* | 7/2019 | Sobol | A61B 5/7267 |

OTHER PUBLICATIONS https://azati.ai/artificial-intelligence-and-machine-learning-for-real-estate/.
https://arxiv.org/pdf/1809.04933.pdf.
https://dspace.mit.edu/bitstream/handle/1721.1/120609/1088413444-MIT.pdf?sequence=1&isAllowed=y.

* cited by examiner

US 11,684,316 B2

ARTIFICIAL INTELLIGENCE SYSTEMS AND METHODS FOR GENERATING LAND RESPONSES FROM BIOLOGICAL EXTRACTIONS

FIELD OF THE INVENTION

The present invention generally relates to the field of artificial intelligence. In particular, the present invention is directed to artificial intelligence systems and methods for generating land responses from biological extractions.

BACKGROUND

Time spent on land chosen without regard to one's composition can have devastating effects. Inadvertently, land may be toxic and may further exacerbate medical conditions and worsen diagnoses. There remains to be seen, a way to be informed about personalized dangers that may be lurking unknown to the average human being.

SUMMARY OF THE DISCLOSURE

In an aspect, an artificial intelligence system for generating land responses from biological extractions, the system comprising a computing device, the computing device designed and configured to retrieve a biological extraction pertaining to a user, wherein the biological extraction contains at least an element of physiological data. The computing device is further configured to locate a land descriptor wherein the land descriptor identifies a property. The computing device is further configured to generate a land machine-learning model, wherein the land machine-learning model utilizes the biological extraction and the land descriptor as an input and outputs property elements. The computing device is further configured to determine the suitability of the property utilizing the output property elements.

In an aspect, an artificial intelligence method of generating land responses from biological extractions, the method comprising retrieving, by a computing device, a biological extraction pertaining to a user, wherein the biological extraction contains at least an element of physiological data. The method comprising locating, by the computing device, a land descriptor wherein the land descriptor identifies a property. The method comprising generating, by the computing device, a land machine-learning model, wherein the land machine-learning model utilizes the biological extraction and the land descriptor as an input and outputs property elements. The method comprising determining, by the computing device, the suitability of the property utilizing the output property elements.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for generating land responses from biological extractions. In an embodiment, a computing device retrieves a biological extraction pertaining to a user, wherein the biological extraction contains at least an element of physiological data. A computing device locates a land descriptor wherein the land descriptor identifies a property. A property may include an industrial property, a commercial property, a personal property and the like. A computing device generates a land machine-learning model, that utilizes a biological extraction and a land descriptor as an input and outputs property elements. A computing device determines the suitability of the property utilizing the output property elements.

Figure 1:
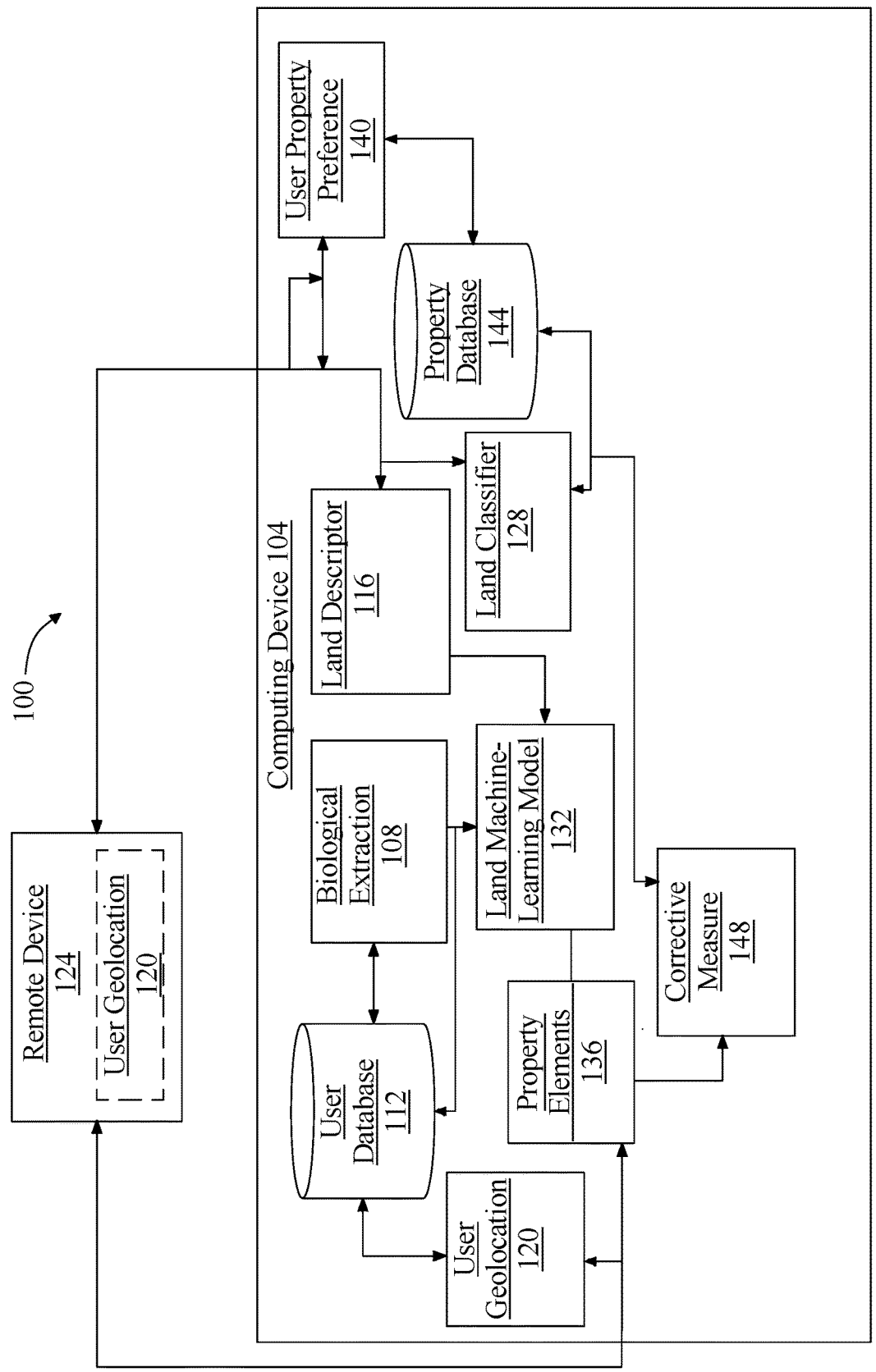
FIG. 1 is a block diagram illustrating an exemplary embodiment of an artificial intelligence system for generating land responses from biological extractions.

Referring now to FIG. 1, an exemplary embodiment of an artificial intelligence system 100 for generating land responses from biological extractions is illustrated. System 100 includes a computing device 104. Computing device 104 may include any computing device 104 as described in this disclosure, including without limitation a microcontroller, microprocessor, digital signal processor (DSP) and/or system on a chip (SoC) as described in this disclosure. Computing device 104 may include, be included in, and/or communicate with a mobile device such as a mobile telephone or smartphone. Computing device 104 may include a single computing device 104 operating independently or may include two or more computing device 104 operating in concert, in parallel, sequentially or the like; two or more computing devices 104 may be included together in a single computing device 104 or in two or more computing devices 104. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices 104, and any combinations thereof. A network may employ a wired and/or a wireless mode of communication.

In general, any network topology may be used. Information (e.g., data, software etc.) may be communicated to and/or from a computer and/or a computing device 104. Computing device 104 may include but is not limited to, for example, a computing device 104 or cluster of computing devices 104 in a first location and a second computing device 104 or cluster of computing devices 104 in a second location. Computing device 104 may include one or more computing devices 104 dedicated to data storage, security, distribution of traffic for load balancing, and the like. Computing device 104 may distribute one or more computing tasks as described below across a plurality of computing devices 104 of computing device 104, which may operate in parallel, in series, redundantly, or in any other manner used for distribution of tasks or memory between computing devices 104. Computing device 104 may be implemented using a "shared nothing" architecture in which data is cached at the worker, in an embodiment, this may enable scalability of system 100 and/or computing device 104.

Continuing to refer to FIG. 1, computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, computing device 104 is configured to retrieve a biological extraction pertaining to a user. Still referring to FIG. 1, computing device 104 may be configured to receive a biological extraction 108 pertaining to a user. A "biological extraction" as used in this disclosure is an element of data including at least an element of user physiological data. As used in this disclosure, "physiological data" is any data indicative of a person's physiological state; physiological state may be evaluated with regard to one or more measures of health of a person's body, one or more systems within a person's body such as a circulatory system, a digestive system, a nervous system, or the like, one or more organs within a person's body, and/or any other subdivision of a person's body useful for diagnostic or prognostic purposes. For instance, and without limitation, a particular set of biomarkers, test results, and/or biochemical information may be recognized in a given medical field as useful for identifying various disease conditions or prognoses within a relevant field. As a non-limiting example, and without limitation, physiological data describing red blood cells, such as red blood cell count, hemoglobin levels, hematocrit, mean corpuscular volume, mean corpuscular hemoglobin, and/or mean corpuscular hemoglobin concentration may be recognized as useful for identifying various conditions such as dehydration, high testosterone, nutrient deficiencies, kidney dysfunction, chronic inflammation, anemia, and/or blood loss.

With continued reference to FIG. 1, physiological state data may include, without limitation, hematological data, such as red blood cell count, which may include a total number of red blood cells in a person's blood and/or in a blood sample, hemoglobin levels, hematocrit representing a percentage of blood in a person and/or sample that is composed of red blood cells, mean corpuscular volume, which may be an estimate of the average red blood cell size, mean corpuscular hemoglobin, which may measure average weight of hemoglobin per red blood cell, mean corpuscular hemoglobin concentration, which may measure an average concentration of hemoglobin in red blood cells, platelet count, mean platelet volume which may measure the average size of platelets, red blood cell distribution width, which measures variation in red blood cell size, absolute neutrophils, which measures the number of neutrophil white blood cells, absolute quantities of lymphocytes such as B-cells, T-cells, Natural Killer Cells, and the like, absolute numbers of monocytes including macrophage precursors, absolute numbers of eosinophils, and/or absolute counts of basophils. Physiological state data may include, without limitation, immune function data such as Interleukine-6 (IL-6), TNF-alpha, systemic inflammatory cytokines, and the like.

Continuing to refer to FIG. 1, physiological state data may include, without limitation, data describing blood-born lipids, including total cholesterol levels, high-density lipoprotein (HDL) cholesterol levels, low-density lipoprotein (LDL) cholesterol levels, very low-density lipoprotein (VLDL) cholesterol levels, levels of triglycerides, and/or any other quantity of any blood-born lipid or lipid-containing substance. Physiological state data may include measures of glucose metabolism such as fasting glucose levels and/or hemoglobin A1-C(HbAlc) levels. Physiological state data may include, without limitation, one or more measures associated with endocrine function, such as without limitation, quantities of dehydroepiandrosterone (DHEAS), DHEA-Sulfate, quantities of cortisol, ratio of DHEAS to cortisol, quantities of testosterone quantities of estrogen, quantities of growth hormone (GH), insulin-like growth factor 1 (IGF-1), quantities of adipokines such as adiponectin, leptin, and/or ghrelin, quantities of somatostatin, progesterone, or the like. Physiological state data may include measures of estimated glomerular filtration rate (eGFR). Physiological state data may include quantities of C-reactive protein, estradiol, ferritin, folate, homocysteine, prostate-specific Ag, thyroid-stimulating hormone, vitamin D, 25 hydroxy, blood urea nitrogen, creatinine, sodium, potassium, chloride, carbon dioxide, uric acid, albumin, globulin, calcium, phosphorus, alkaline phosphatase, alanine amino transferase, aspartate amino transferase, lactate dehydrogenase (LDH), bilirubin, gamma-glutamyl transferase (GGT), iron, and/or total iron binding capacity (TIBC), or the like. Physiological state data may include antinuclear antibody levels. Physiological state data may include aluminum levels. Physiological state data may include arsenic levels. Physiological state data may include levels of fibrinogen, plasma cystatin C, and/or brain natriuretic peptide.

Continuing to refer to FIG. 1, physiological state data may include measures of lung function such as forced expiratory volume, one second (FEV-1) which measures how much air can be exhaled in one second following a deep inhalation, forced vital capacity (FVC), which measures the volume of air that may be contained in the lungs. Physiological state data may include a measurement blood pressure, including without limitation systolic and diastolic blood pressure. Physiological state data may include a measure of waist circumference. Physiological state data may include body mass index (BMI). Physiological state data may include one or more measures of bone mass and/or density such as dual-energy x-ray absorptiometry. Physiological state data may include one or more measures of muscle mass. Physiological state data may include one or more measures of physical capability such as without limitation measures of grip strength, evaluations of standing balance, evaluations of gait speed, pegboard tests, timed up and go tests, and/or chair rising tests.

Still viewing FIG. 1, physiological state data may include one or more measures of cognitive function, including without limitation Rey auditory verbal learning test results, California verbal learning test results, NIH toolbox picture sequence memory test, Digital symbol coding evaluations, and/or Verbal fluency evaluations. Physiological state data may include one or more evaluations of sensory ability, including measures of audition, vision, olfaction, gustation, vestibular function and pain.

Continuing to refer to FIG. 1, physiological state data may include psychological data. Psychological data may include any data generated using psychological, neuro-psychological, and/or cognitive evaluations, as well as diagnostic screening tests, personality tests, personal compatibility tests, or the like; such data may include, without limitation, numerical score data entered by an evaluating professional and/or by a subject performing a self-test such as a computerized questionnaire. Psychological data may include textual, video, or image data describing testing, analysis, and/or conclusions entered by a medical professional such as without limitation a psychologist, psychiatrist, psychotherapist, social worker, a medical doctor, or the like. Psychological data may include data gathered from user interactions with persons, documents, and/or computing devices 104; for instance, user patterns of purchases, including electronic purchases, communication such as via chat-rooms or the like, any textual, image, video, and/or data produced by the subject, any textual image, video and/or other data depicting and/or describing the subject, or the like. Any psychological data and/or data used to generate psychological data may be analyzed using machine-learning and/or language processing module as described in this disclosure. As a non-limiting example, biological extraction 108 may include a psychological profile; the psychological profile may be obtained utilizing a questionnaire performed by the user.

Still referring to FIG. 1, physiological state data may include genomic data, including deoxyribonucleic acid (DNA) samples and/or sequences, such as without limitation DNA sequences or other genetic sequences contained in one or more chromosomes in human cells. Genomic data may include, without limitation, ribonucleic acid (RNA) samples and/or sequences, such as samples and/or sequences of messenger RNA (mRNA) or the like taken from human cells. Genetic data may include telomere lengths. Genomic data may include epigenetic data including data describing one or more states of methylation of genetic material. Physiological state data may include proteomic data, which as used herein is data describing all proteins produced and/or modified by an organism, colony of organisms, or system of organisms, and/or a subset thereof. Physiological state data may include data concerning a microbiome of a person, which as used herein includes any data describing any microorganism and/or combination of microorganisms living on or within a person, including without limitation biomarkers, genomic data, proteomic data, and/or any other metabolic or biochemical data useful for analysis of the effect of such microorganisms on other physiological state data of a person, as described in further detail below.

With continuing reference to FIG. 1, physiological state data may include one or more user-entered descriptions of a person's physiological state. One or more user-entered descriptions may include, without limitation, user descriptions of symptoms, which may include without limitation current or past physical, psychological, perceptual, and/or neurological symptoms, user descriptions of current or past physical, emotional, and/or psychological problems and/or concerns, user descriptions of past or current treatments, including therapies, nutritional regimens, exercise regimens, pharmaceuticals or the like, or any other user-entered data that a user may provide to a medical professional when seeking treatment and/or evaluation, and/or in response to medical intake papers, questionnaires, questions from medical professionals, or the like. Physiological state data may include any physiological state data, as described above, describing any multicellular organism living in or on a person including any parasitic and/or symbiotic organisms living in or on the persons; non-limiting examples may include mites, nematodes, flatworms, or the like. Examples of physiological state data described in this disclosure are presented for illustrative purposes only and are not meant to be exhaustive.

With continued reference to FIG. 1, physiological data may include, without limitation any result of any medical test, physiological assessment, cognitive assessment, psychological assessment, or the like. System 100 may receive at least a physiological data from one or more other devices after performance; system 100 may alternatively or additionally perform one or more assessments and/or tests to obtain at least a physiological data, and/or one or more portions thereof, on system 100. For instance, at least physiological data may include or more entries by a user in a form or similar graphical user interface object; one or more entries may include, without limitation, user responses to questions on a psychological, behavioral, personality, or cognitive test. For instance, at least a server may present to user a set of assessment questions designed or intended to evaluate a current state of mind of the user, a current psychological state of the user, a personality trait of the user, or the like; at least a server may provide user-entered responses to such questions directly as at least a physiological data and/or may perform one or more calculations or other algorithms to derive a score or other result of an assessment as specified by one or more testing protocols, such as automated calculation of a Stanford-Binet and/or Wechsler scale for IQ testing, a personality test scoring such as a Myers-Briggs test protocol, or other assessments that may occur to persons skilled in the art upon reviewing the entirety of this disclosure.

With continued reference to FIG. 1, assessment and/or self-assessment data, and/or automated or other assessment results, obtained from a third-party device 116; third-party device 116 may include, without limitation, a server or other device (not shown) that performs automated cognitive, psychological, behavioral, personality, or other assessments. Third-party device 116 may include a device operated by an informed advisor. An informed advisor may include any medical professional who may assist and/or participate in the medical treatment of a user. An informed advisor may include a medical doctor, nurse, physician assistant, pharmacist, yoga instructor, nutritionist, spiritual healer, meditation teacher, fitness coach, health coach, life coach, and the like.

With continued reference to FIG. 1, physiological data may include data describing one or more test results, including results of mobility tests, stress tests, dexterity tests, endocrinal tests, genetic tests, and/or electromyographic tests, biopsies, radiological tests, genetic tests, and/or sensory tests. Persons skilled in the art, upon reviewing the entirety of this disclosure, will be aware of various additional examples of at least a physiological sample consistent with this disclosure.

With continued reference to FIG. 1, physiological data may include one or more user body measurements. A "user body measurement" as used in this disclosure, includes a measurable indicator of the severity, absence, and/or presence of a disease state. A "disease state" as used in this disclosure, includes any harmful deviation from the normal structural and/or function state of a human being. A disease state may include any medical condition and may be associated with specific symptoms and signs. A disease state may be classified into different types including infectious diseases, deficiency diseases, hereditary diseases, and/or physiological diseases. For instance and without limitation, internal dysfunction of the immune system may produce a variety of different diseases including immunodeficiency, hypersensitivity, allergies, and/or autoimmune disorders.

With continued reference to FIG. 1, user body measurements may be related to particular dimensions of the human body. A "dimension of the human body" as used in this disclosure, includes one or more functional body systems that are impaired by disease in a human body and/or animal body. Functional body systems may include one or more body systems recognized as attributing to root causes of disease by functional medicine practitioners and experts. A "root cause" as used in this disclosure, includes any chain of causation describing underlying reasons for a particular disease state and/or medical condition instead of focusing solely on symptomatology reversal. Root cause may include chains of causation developed by functional medicine practices that may focus on disease causation and reversal. For instance and without limitation, a medical condition such as diabetes may include a chain of causation that does not include solely impaired sugar metabolism but that also includes impaired hormone systems including insulin resistance, high cortisol, less than optimal thyroid production, and low sex hormones. Diabetes may include further chains of causation that include inflammation, poor diet, delayed food allergies, leaky gut, oxidative stress, damage to cell membranes, and dysbiosis. Dimensions of the human body may include but are not limited to epigenetics, gut-wall, microbiome, nutrients, genetics, and/or metabolism.

With continued reference to FIG. 1, epigenetic, as used herein, includes any user body measurements describing changes to a genome that do not involve corresponding changes in nucleotide sequence. Epigenetic body measurement may include data describing any heritable phenotypic. Phenotype, as used herein, include any observable trait of a user including morphology, physical form, and structure. Phenotype may include a user's biochemical and physiological properties, behavior, and products of behavior. Behavioral phenotypes may include cognitive, personality, and behavior patterns. This may include effects on cellular and physiological phenotypic traits that may occur due to external or environmental factors. For example, DNA methylation and histone modification may alter phenotypic expression of genes without altering underlying DNA sequence. Epigenetic body measurements may include data describing one or more states of methylation of genetic material.

With continued reference to FIG. 1, gut-wall, as used herein, includes the space surrounding the lumen of the gastrointestinal tract that is composed of four layers including the mucosa, submucosa, muscular layer, and serosa. The mucosa contains the gut epithelium that is composed of goblet cells that function to secrete mucus, which aids in lubricating the passage of food throughout the digestive tract. The goblet cells also aid in protecting the intestinal wall from destruction by digestive enzymes. The mucosa includes villi or folds of the mucosa located in the small intestine that increase the surface area of the intestine. The villi contain a lacteal, that is a vessel connected to the lymph system that aids in removal of lipids and tissue fluids. Villi may contain microvilli that increase the surface area over which absorption can take place. The large intestine lack villi and instead a flat surface containing goblet cells are present.

With continued reference to FIG. 1, gut-wall includes the submucosa, which contains nerves, blood vessels, and elastic fibers containing collagen. Elastic fibers contained within the submucosa aid in stretching the gastrointestinal tract with increased capacity while also maintaining the shape of the intestine. Gut-wall includes muscular layer which contains smooth muscle that aids in peristalsis and the movement of digested material out of and along the gut. Gut-wall includes the serosa which is composed of connective tissue and coated in mucus to prevent friction damage from the intestine rubbing against other tissue. Mesenteries are also found in the serosa and suspend the intestine in the abdominal cavity to stop it from being disturbed when a person is physically active.

With continued reference to FIG. 1, gut-wall body measurement may include data describing one or more test results including results of gut-wall function, gut-wall integrity, gut-wall strength, gut-wall absorption, gut-wall permeability, intestinal absorption, gut-wall barrier function, gut-wall absorption of bacteria, gut-wall malabsorption, gut-wall gastrointestinal imbalances and the like.

With continued reference to FIG. 1, gut-wall body measurement may include any data describing blood test results of creatinine levels, lactulose levels, zonulin levels, and mannitol levels. Gut-wall body measurement may include blood test results of specific gut-wall body measurements including d-lactate, endotoxin lipopolysaccharide (LPS) Gut-wall body measurement may include data breath tests measuring lactulose, hydrogen, methane, lactose, and the like. Gut-wall body measurement may include blood test results describing blood chemistry levels of albumin, bilirubin, complete blood count, electrolytes, minerals, sodium, potassium, calcium, glucose, blood clotting factors, With continued reference to FIG. 1, gut-wall body measurement may include one or more stool test results describing presence or absence of parasites, firmicutes, Bacteroidetes, absorption, inflammation, food sensitivities. Stool test results may describe presence, absence, and/or measurement of acetate, aerobic bacterial cultures, anerobic bacterial cultures, fecal short chain fatty acids, beta-glucuronidase, cholesterol, chymotrypsin, fecal color, cryptosporidium EIA, *Entamoeba histolytica*, fecal lactoferrin, *Giardia lamblia* EIA, long chain fatty acids, meat fibers and vegetable fibers, mucus, occult blood, parasite identification, phospholipids, propionate, putrefactive short chain fatty acids, total fecal fat, triglycerides, yeast culture, n-butyrate, pH and the like.

With continued reference to FIG. 1, gut-wall body measurement may include one or more stool test results describing presence, absence, and/or measurement of microorganisms including bacteria, archaea, fungi, protozoa, algae, viruses, parasites, worms, and the like. Stool test results may contain species such as *Bifidobacterium* species, *campylobacter* species, *Clostridium difficile, cryptosporidium* species, *Cyclospora cayetanensis, Cryptosporidium* EIA, *Dientamoeba fragilis, Entamoeba histolytica, Escherichia coli, Entamoeba histolytica, Giardia, H. pylori, Candida albicans, Lactobacillus* species, worms, macroscopic worms, mycology, protozoa, Shiga toxin *E. coli*, and the like.

With continued reference to FIG. 1, gut-wall body measurement may include one or more microscopic ova exam results, microscopic parasite exam results, protozoan polymerase chain reaction test results and the like. Gut-wall body measurement may include enzyme-linked immunosorbent assay (ELISA) test results describing immunoglobulin G (Ig G) food antibody results, immunoglobulin E (Ig E) food antibody results, Ig E mold results, IgG spice and herb results. Gut-wall body measurement may include measurements of calprotectin, eosinophil protein x (EPX), stool weight, pancreatic elastase, total urine volume, blood creatinine levels, blood lactulose levels, blood mannitol levels.

With continued reference to FIG. 1, gut-wall body measurement may include one or more elements of data describing one or more procedures examining gut including for example colonoscopy, endoscopy, large and small molecule challenge and subsequent urinary recovery using large molecules such as lactulose, polyethylene glycol-3350, and small molecules such as mannitol, L-rhamnose, polyethyleneglycol-400. Gut-wall body measurement may include data describing one or more images such as x-ray, MRI, CT scan, ultrasound, standard barium follow-through examination, barium enema, barium with contract, MRI fluoroscopy, positron emission tomography 9PET), diffusion-weighted MRI imaging, and the like.

With continued reference to FIG. 1, microbiome, as used herein, includes ecological community of commensal, symbiotic, and pathogenic microorganisms that reside on or within any of a number of human tissues and biofluids. For example, human tissues and biofluids may include the skin, mammary glands, placenta, seminal fluid, uterus, vagina, ovarian follicles, lung, saliva, oral mucosa, conjunctiva, biliary, and gastrointestinal tracts. Microbiome may include for example, bacteria, archaea, protists, fungi, and viruses. Microbiome may include commensal organisms that exist within a human being without causing harm or disease. Microbiome may include organisms that are not harmful but rather harm the human when they produce toxic metabolites such as trimethylamine. Microbiome may include pathogenic organisms that cause host damage through virulence factors such as producing toxic by-products. Microbiome may include populations of microbes such as bacteria and yeasts that may inhabit the skin and mucosal surfaces in various parts of the body. Bacteria may include for example Firmicutes species, Bacteroidetes species, Proteobacteria species, Verrumicrobia species, Actinobacteria species, Fusobacteria species, Cyanobacteria species and the like. Archaea may include methanogens such as *Methanobrevibacter* smithies' and Methanosphaera stadtmanae. Fungi may include *Candida* species and *Malassezia* species. Viruses may include bacteriophages. Microbiome species may vary in different locations throughout the body. For example, the genitourinary system may contain a high prevalence of *Lactobacillus* species while the gastrointestinal tract may contain a high prevalence of *Bifidobacterium* species while the lung may contain a high prevalence of *Streptococcus* and *Staphylococcus* species.

With continued reference to FIG. 1, microbiome body measurement may include one or more stool test results describing presence, absence, and/or measurement of microorganisms including bacteria, archaea, fungi, protozoa, algae, viruses, parasites, worms, and the like. Stool test results may contain species such as Ackerman's muciniphila, Anaerotruncus colihominis, bacteriology, *Bacteroides vulgates', Bacteroides-Prevotella, Barnesiella* species, *Bifidobacterium longarm, Bifidobacterium* species, *Butyrivbrio crossotus, Clostridium* species, *Collinsella aerofaciens*, fecal color, fecal consistency, *Coprococcus eutactus, Desulfovibrio piger, Escherichia coli, Faecalibacterium prausnitzii*, Fecal occult blood, Firmicutes to Bacteroidetes ratio, *Fusobacterium* species, *Lactobacillus* species, *Methanobrevibacter smithii*, yeast minimum inhibitory concentration, bacteria minimum inhibitory concentration, yeast mycology, fungi mycology, *Odoribacter* species, *Oxalobacter formigenes*, parasitology, *Prevotella* species, *Pseudoflavonifractor* species, *Roseburia* species, *Ruminococcus* species, *Veillonella* species and the like.

With continued reference to FIG. 1, microbiome body measurement may include one or more stools results that identify all microorganisms living a user's gut including bacteria, viruses, archaea, yeast, fungi, parasites, and bacteriophages. Microbiome body measurement may include DNA and RNA sequences from live microorganisms that may impact a user's health. Microbiome body measurement may include high resolution of both species and strains of all microorganisms. Microbiome body measurement may include data describing current microbe activity. Microbiome body measurement may include expression of levels of active microbial gene functions. Microbiome body measurement may include descriptions of sources of disease-causing microorganisms, such as viruses found in the gastrointestinal tract such as raspberry bushy swarf virus from consuming contaminated raspberries or Pepino mosaic virus from consuming contaminated tomatoes.

With continued reference to FIG. 1, microbiome body measurement may include one or more blood test results that identify metabolites produced by microorganisms. Metabolites may include for example, indole-3-propionic acid, indole-3-lactic acid, indole-3-acetic acid, tryptophan, serotonin, kynurenine, total indoxyl sulfate, tyrosine, xanthine, 3-methylxanthine, uric acid, and the like.

With continued reference to FIG. 1, microbiome body measurement may include one or more breath test results that identify certain strains of microorganisms that may be present in certain areas of a user's body. This may include for example, lactose intolerance breath tests, methane-based breath tests, hydrogen-based breath tests, fructose-based breath tests, *Helicobacter pylori* breath test, fructose intolerance breath test, bacterial overgrowth syndrome breath tests and the like.

With continued reference to FIG. 1, microbiome body measurement may include one or more urinary analysis results for certain microbial strains present in urine. This may include for example, urinalysis that examines urine specific gravity, urine cytology, urine sodium, urine culture, urinary calcium, urinary hematuria, urinary glucose levels, urinary acidity, urinary protein, urinary nitrites, bilirubin, red blood cell urinalysis, and the like.

With continued reference to FIG. 1, nutrient as used herein, includes any substance required by the human body to function. Nutrients may include carbohydrates, protein, lipids, vitamins, minerals, antioxidants, fatty acids, amino acids, and the like. Nutrients may include for example vitamins such as thiamine, riboflavin, niacin, pantothenic acid, pyridoxine, biotin, folate, cobalamin, Vitamin C, Vitamin A, Vitamin D, Vitamin E, and Vitamin K. Nutrients may include for example minerals such as sodium, chloride, potassium, calcium, phosphorous, magnesium, sulfur, iron, zinc, iodine, selenium, copper, manganese, fluoride, chromium, molybdenum, nickel, aluminum, silicon, vanadium, arsenic, and boron.

With continued reference to FIG. 1, nutrients may include extracellular nutrients that are free floating in blood and exist outside of cells. Extracellular nutrients may be located in serum. Nutrients may include intracellular nutrients which may be absorbed by cells including white blood cells and red blood cells.

With continued reference to FIG. 1, nutrient body measurement may include one or more blood test results that identify extracellular and intracellular levels of nutrients. Nutrient body measurement may include blood test results that identify serum, white blood cell, and red blood cell levels of nutrients. For example, nutrient body measurement may include serum, white blood cell, and red blood cell levels of micronutrients such as Vitamin A, Vitamin B1, Vitamin B2, Vitamin B3, Vitamin B6, Vitamin B12, Vitamin B5, Vitamin C, Vitamin D, Vitamin E, Vitamin K1, Vitamin K2, and folate.

With continued reference to FIG. 1, nutrient body measurement may include one or more blood test results that identify serum, white blood cell and red blood cell levels of nutrients such as calcium, manganese, zinc, copper, chromium, iron, magnesium, copper to zinc ratio, choline, inositol, carnitine, methylmalonic acid (MMA), sodium, potassium, asparagine, glutamine, serine, coenzyme q10, cysteine, alpha lipoic acid, glutathione, selenium, eicosapentaenoic acid (EPA), docosahexaenoic acid (DHA), docosapentaenoic acid (DPA), total omega-3, lauric acid, arachidonic acid, oleic acid, total omega 6, and omega 3 index.

With continued reference to FIG. 1, nutrient body measurement may include one or more salivary test results that identify levels of nutrients including any of the nutrients as described herein. Nutrient body measurement may include hair analysis of levels of nutrients including any of the nutrients as described herein.

With continued reference to FIG. 1, genetic as used herein, includes any inherited trait. Inherited traits may include genetic material contained with DNA including for example, nucleotides. Nucleotides include adenine (A), cytosine (C), guanine (G), and thymine (T). Genetic information may be contained within the specific sequence of an individual's nucleotides and sequence throughout a gene or DNA chain. Genetics may include how a particular genetic sequence may contribute to a tendency to develop a certain disease such as cancer or Alzheimer's disease.

With continued reference to FIG. 1, genetic body measurement may include one or more results from one or more blood tests, hair tests, skin tests, urine, amniotic fluid, buccal swabs and/or tissue test to identify a user's particular sequence of nucleotides, genes, chromosomes, and/or proteins. Genetic body measurement may include tests that example genetic changes that may lead to genetic disorders. Genetic body measurement may detect genetic changes such as deletion of genetic material or pieces of chromosomes that may cause Duchenne Muscular Dystrophy. Genetic body measurement may detect genetic changes such as insertion of genetic material into DNA or a gene such as the BRCA1 gene that is associated with an increased risk of breast and ovarian cancer due to insertion of 2 extra nucleotides. Genetic body measurement may include a genetic change such as a genetic substitution from a piece of genetic material that replaces another as seen with sickle cell anemia where one nucleotide is substituted for another. Genetic body measurement may detect a genetic change such as a duplication when extra genetic material is duplicated one or more times within a person's genome such as with Charcot-Marie Tooth disease type 1. Genetic body measurement may include a genetic change such as an amplification when there is more than a normal number of copies of a gene in a cell such as HER2 amplification in cancer cells. Genetic body measurement may include a genetic change such as a chromosomal translocation when pieces of chromosomes break off and reattach to another chromosome such as with the BCR-ABL1 gene sequence that is formed when pieces of chromosome 9 and chromosome 22 break off and switch places. Genetic body measurement may include a genetic change such as an inversion when one chromosome experiences two breaks and the middle piece is flipped or inverted before reattaching. Genetic body measurement may include a repeat such as when regions of DNA contain a sequence of nucleotides that repeat a number of times such as for example in Huntington's disease or Fragile X syndrome. Genetic body measurement may include a genetic change such as a trisomy when there are three chromosomes instead of the usual pair as seen with Down syndrome with a trisomy of chromosome 21, Edwards syndrome with a trisomy at chromosome 18 or Patau syndrome with a trisomy at chromosome 13. Genetic body measurement may include a genetic change such as monosomy such as when there is an absence of a chromosome instead of a pair, such as in Turner syndrome.

With continued reference to FIG. 1, genetic body measurement may include an analysis of COMT gene that is responsible for producing enzymes that metabolize neurotransmitters. Genetic body measurement may include an analysis of DRD2 gene that produces dopamine receptors in the brain. Genetic body measurement may include an analysis of ADRA2B gene that produces receptors for noradrenaline. Genetic body measurement may include an analysis of 5-HTTLPR gene that produces receptors for serotonin. Genetic body measurement may include an analysis of BDNF gene that produces brain derived neurotrophic factor. Genetic body measurement may include an analysis of 9p21 gene that is associated with cardiovascular disease risk. Genetic body measurement may include an analysis of APOE gene that is involved in the transportation of blood lipids such as cholesterol. Genetic body measurement may include an analysis of NOS3 gene that is involved in producing enzymes involved in regulating vasodilation and vasoconstriction of blood vessels.

With continued reference to FIG. 1, genetic body measurement may include ACE gene that is involved in producing enzymes that regulate blood pressure. Genetic body measurement may include SLCO1B1 gene that directs pharmaceutical compounds such as statins into cells. Genetic body measurement may include FUT2 gene that produces enzymes that aid in absorption of Vitamin B12 from digestive tract. Genetic body measurement may include MTHFR gene that is responsible for producing enzymes that aid in metabolism and utilization of Vitamin B9 or folate. Genetic body measurement may include SHMT1 gene that aids in production and utilization of Vitamin B9 or folate. Genetic body measurement may include MTRR gene that produces enzymes that aid in metabolism and utilization of Vitamin B12. Genetic body measurement may include MTR gene that produces enzymes that aid in metabolism and utilization of Vitamin B12. Genetic body measurement may include FTO gene that aids in feelings of satiety or fulness after eating. Genetic body measurement may include MC4R gene that aids in producing hunger cues and hunger triggers. Genetic body measurement may include APOA2 gene that directs body to produce ApoA2 thereby affecting absorption of saturated fats. Genetic body measurement may include UCP1 gene that aids in controlling metabolic rate and thermoregulation of body. Genetic body measurement may include TCF7L2 gene that regulates insulin secretion. Genetic body measurement may include AMY1 gene that aids in digestion of starchy foods. Genetic body measurement may include MCM6 gene that controls production of lactase enzyme that aids in digesting lactose found in dairy products. Genetic body measurement may include BCMO1 gene that aids in producing enzymes that aid in metabolism and activation of Vitamin A. Genetic body measurement may include SLC23A1 gene that produce and transport Vitamin C. Genetic body measurement may include CYP2R1 gene that produce enzymes involved in production and activation of Vitamin D. Genetic body measurement may include GC gene that produce and transport Vitamin D. Genetic body measurement may include CYP1A2 gene that aid in metabolism and elimination of caffeine. Genetic body measurement may include CYP17A1 gene that produce enzymes that convert progesterone into androgens such as androstenedione, androstendiol, dehydroepiandrosterone, and testosterone.

With continued reference to FIG. 1, genetic body measurement may include CYP19A1 gene that produce enzymes that convert androgens such as androstenedione and testosterone into estrogens including estradiol and estrone. Genetic body measurement may include SRD5A2 gene that aids in production of enzymes that convert testosterone into dihydrotestosterone. Genetic body measurement may include UFT2B17 gene that produces enzymes that metabolize testosterone and dihydrotestosterone. Genetic body measurement may include CYP1A1 gene that produces enzymes that metabolize estrogens into 2 hydroxy-estrogen. Genetic body measurement may include CYP1B1 gene that produces enzymes that metabolize estrogens into 4 hydroxy-estrogen. Genetic body measurement may include CYP3A4 gene that produces enzymes that metabolize estrogen into 16 hydroxy-estrogen. Genetic body measurement may include COMT gene that produces enzymes that metabolize 2 hydroxy-estrogen and 4 hydroxy-estrogen into methoxy estrogen. Genetic body measurement may include GSTT1 gene that produces enzymes that eliminate toxic by-products generated from metabolism of estrogens. Genetic body measurement may include GSTM1 gene that produces enzymes responsible for eliminating harmful by-products generated from metabolism of estrogens. Genetic body measurement may include GSTP1 gene that produces enzymes that eliminate harmful by-products generated from metabolism of estrogens. Genetic body measurement may include SOD2 gene that produces enzymes that eliminate oxidant by-products generated from metabolism of estrogens.

With continued reference to FIG. 1, metabolic, as used herein, includes any process that converts food and nutrition into energy. Metabolic may include biochemical processes that occur within the body. Metabolic body measurement may include blood tests, hair tests, skin tests, amniotic fluid, buccal swabs and/or tissue test to identify a user's metabolism. Metabolic body measurement may include blood tests that examine glucose levels, electrolytes, fluid balance, kidney function, and liver function. Metabolic body measurement may include blood tests that examine calcium levels, albumin, total protein, chloride levels, sodium levels, potassium levels, carbon dioxide levels, bicarbonate levels, blood urea nitrogen, creatinine, alkaline phosphatase, alanine amino transferase, aspartate amino transferase, bilirubin, and the like.

With continued reference to FIG. 1, metabolic body measurement may include one or more blood, saliva, hair, urine, skin, and/or buccal swabs that examine levels of hormones within the body such as 11-hydroxy-androsterone, 11-hydroxy-etiocholanolone, 11-keto-androsterone, 11-keto-etiocholanolone, 16 alpha-hydroxyestrone, 2-hydroxyestrone, 4-hydroxyestrone, 4-methoxyestrone, androstanediol, androsterone, creatinine, DHEA, estradiol, estriol, estrone, etiocholanolone, pregnanediol, pregnanestriol, specific gravity, testosterone, tetrahydrocortisol, tetrahydrocrotisone, tetrahydrodeoxycortisol, allo-tetrahydrocortisol.

With continued reference to FIG. 1, metabolic body measurement may include one or more metabolic rate test results such as breath tests that may analyze a user's resting metabolic rate or number of calories that a user's body burns each day rest. Metabolic body measurement may include one or more vital signs including blood pressure, breathing rate, pulse rate, temperature, and the like. Metabolic body measurement may include blood tests such as a lipid panel such as low density lipoprotein (LDL), high density lipoprotein (HDL), triglycerides, total cholesterol, ratios of lipid levels such as total cholesterol to HDL ratio, insulin sensitivity test, fasting glucose test, Hemoglobin A1C test, adipokines such as leptin and adiponectin, neuropeptides such as ghrelin, pro-inflammatory cytokines such as interleukin 6 or tumor necrosis factor alpha, anti-inflammatory cytokines such as interleukin 10, markers of antioxidant status such as oxidized low-density lipoprotein, uric acid, paraoxonase 1. Persons skilled in the art, upon reviewing the entirety of this disclosure, will be aware of various additional examples of physiological state data that may be used consistently with descriptions of systems and methods as provided in this disclosure.

With continued reference to FIG. 1, physiological data may be obtained from a physically extracted sample. A "physical sample" as used in this example, may include any sample obtained from a human body of a user. A physical sample may be obtained from a bodily fluid and/or tissue analysis such as a blood sample, tissue, sample, buccal swab, mucous sample, stool sample, hair sample, fingernail sample and the like. A physical sample may be obtained from a device in contact with a human body of a user such as a microchip embedded in a user's skin, a sensor in contact with a user's skin, a sensor located on a user's tooth, and the like. Physiological data may be obtained from a physically extracted sample. A physical sample may include a signal from a sensor configured to detect physiological data of a user and record physiological data as a function of the signal. A sensor may include any medical sensor and/or medical device configured to capture sensor data concerning a patient, including any scanning, radiological and/or imaging device such as without limitation x-ray equipment, computer assisted tomography (CAT) scan equipment, positron emission tomography (PET) scan equipment, any form of magnetic resonance imagery (MM) equipment, ultrasound equipment, optical scanning equipment such as photo-plethysmographic equipment, or the like. A sensor may include any electromagnetic sensor, including without limitation electroencephalographic sensors, magnetoencephalographic sensors, electrocardiographic sensors, electromyographic sensors, or the like. A sensor may include a temperature sensor. A sensor may include any sensor that may be included in a mobile device and/or wearable device, including without limitation a motion sensor such as an inertial measurement unit (IMU), one or more accelerometers, one or more gyroscopes, one or more magnetometers, or the like. At least a wearable and/or mobile device sensor may capture step, gait, and/or other mobility data, as well as data describing activity levels and/or physical fitness. At least a wearable and/or mobile device sensor may detect heart rate or the like. A sensor may detect any hematological parameter including blood oxygen level, pulse rate, heart rate, pulse rhythm, blood sugar, and/or blood pressure. A sensor may be configured to detect internal and/or external biomarkers and/or readings. A sensor may be a part of system 100 or may be a separate device in communication with system 100. User data may include a profile, such as a psychological profile, generated using previous item selections by the user; profile may include, without limitation, a set of actions and/or navigational actions performed as described in further detail below, which may be combined with biological extraction 108 data and/or other user data for processes such as classification to user sets as described in further detail below.

Still referring to FIG. 1, retrieval of biological extraction 108 may include, without limitation, reception of biological extraction 108 from another computing device 104 such as a device operated by a medical and/or diagnostic professional and/or entity, a user client device, and/or any device suitable for use as a third-party device as described in further detail below. Biological extraction 108 may be received via a questionnaire posted and/or displayed on a third-party device as described below, inputs to which may be processed as described in further detail below. Alternatively or additionally, biological extraction 108 may be stored in and/or retrieved from a user database 112. User database 112 may include any data structure for ordered storage and retrieval of data, which may be implemented as a hardware or software module. A user database 112 may be implemented, without limitation, as a relational database, a key-value retrieval datastore such as a NOSQL database, or any other format or structure for use as a datastore that a person skilled in the art would recognize as suitable upon review of the entirety of this disclosure. A user database 112 may include a plurality of data entries and/or records corresponding to one or more biological extractions as described above. Data entries in a user database 112 may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a user database 112 may reflect categories, cohorts, and/or populations of data consistently with this disclosure. User database 112 may be located in memory of computing device 104 and/or on another device in and/or in communication with system 100.

With continued reference to FIG. 1, and as noted above, retrieval of biological extraction may be performed multiple sequential and/or concurrent times, and any process using biological extraction as described below may be performed multiple sequential and/or concurrent times; likewise, biological extract may include multiple elements of physiological data, which may be used in combination for any determination and/or other processes as described below.

With continued reference to FIG. 1, computing device 104 is configured to locate a land descriptor 116. A "land descriptor," as used in this disclosure, is data describing a location. A land descriptor 116 may contain a description of a structure, including any residential structure, any commercial structure, any industrial structure, and/or vacant land. A residential structure may include a description of a location that includes the physical address indicating the location of a residence such as a single family detached house, an apartment, a bungalow, a cabin, a carriage house, a castle, a cottage, a cabin, a chalet, a multi-family residence, a mobile home, a condominium, a co-op, a palace, a chateau, a villa, a manor, a water residence, a houseboat and the like. A commercial structure may include any building and/or land intended to generate a profit such as from capital gains or rental income. A commercial structure may include a shopping center, strip mall, medical building, educational building, hotel, office, and/or apartment building. An industrial structure may include manufacturing buildings, warehouses, and/or properties. An industrial structure may be utilized for research, production, storage, and/or distribution of goods. Vacant land includes any land that does not contain any structures or buildings and may not be in use. An address may include information describing the particulars where a structure such as a residence may be found including the street name, street number, city, state, and zip code where a structure is located. A land descriptor 116 may contain a description of a location that includes a geographical location such as a particular state within the United States such as Texas or Louisiana. A land descriptor 116 may contain a description of a geographical region such as the Northeast which encompasses Connecticut, Maine, Massachusetts, New Hampshire, Rhode Island, Vermont, New Jersey, New York and Pennsylvania. A land descriptor 116 may contain a description of a geographical region such as the Great Appalachian Valley or the Ohio Valley. A land descriptor 116 may contain a description of a location that designates a particular region such as a town, county, and/or city.

With continued reference to FIG. 1, computing device 104 may locate a land descriptor 116 as a function of a user geolocation 120. A "user geolocation," as used in this disclosure, is data identifying the real-world geographical location of a user. A user geolocation 120 may be obtained from a radar source, a remote device 124 such as a mobile phone, and/or internet connected device location. A user geolocation 120 may include a global positioning system (GPS) of a user. A user geolocation 120 may include geographic coordinates that may specify the latitude and longitude of a particular location where a user is located. In an embodiment, computing device 104 may receive a user geolocation 120 from a remote device 124 operated by a user. Remote device 124 may include without limitation, a display in communication with computing device 104, where a display may include any display as described herein. Remote device 124 may include an additional computing device, such as a mobile device, laptop, desktop, computer and the like. Computing device 104 may locate a land descriptor 116 utilizing a user questionnaire response that contains user preferences in response to an ideal land descriptor 116. A questionnaire may contain a series of one or more inputs from a user, describing a user's desired land descriptor 116. For example, a questionnaire response may describe a user's desire to live within walking distance of fresh sea air. In yet another non-limiting example, a questionnaire response may describe a user's desire to locate a house that has a minimum of five bedrooms because the user likes to host parties and have guests sleep over.

With continued reference to FIG. 1, computing device 104 may identify a land descriptor 116 using a land classifier

128. A "classifier," as used in this disclosure, is a machine-learning model, such as a mathematical model, neural net, or program generated by a machine learning algorithm known as a "classification algorithm," as described in further detail below, that sorts inputs into categories or bins of data, outputting the categories or bins of data and/or labels associated therewith. Land classifier 128, utilizes a biological extraction pertaining to a user as an input and outputs a land descriptor 116. Computing device 104 may generate land classifier 128 using a classification algorithm, defined as a process whereby a computing device 104 derives a classifier from training data. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers.

With continued reference to FIG. 1, "training data," as used in this disclosure, is data containing correlations that a machine-learning process may use to model relationships between two or more categories of data elements. For instance, and without limitation, training data may include a plurality of data entries, each entry representing a set of data elements that were recorded, received, and/or generated together; data elements may be correlated by shared existence in a given data entry, by proximity in a given data entry, or the like. Multiple data entries in training data may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data according to various correlations; correlations may indicate causative and/or predictive links between categories of data elements, which may be modeled as relationships such as mathematical relationships by machine-learning processes as described in further detail below. Training data may be formatted and/or organized by categories of data elements, for instance by associating data elements with one or more descriptors corresponding to categories of data elements. As a non-limiting example, training data may include data entered in standardized forms by persons or processes, such that entry of a given data element in a given field in a form may be mapped to one or more descriptors of categories. Elements in training data may be linked to descriptors of categories by tags, tokens, or other data elements; for instance, and without limitation, training data may be provided in fixed-length formats, formats linking positions of data to categories such as comma-separated value (CSV) formats and/or self-describing formats such as extensible markup language (XML), enabling processes or devices to detect categories of data.

Alternatively or additionally, and still referring to FIG. 1, training data may include one or more elements that are not categorized; that is, training data may not be formatted or contain descriptors for some elements of data. Machine-learning algorithms and/or other processes may sort training data according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data to be made applicable for two or more distinct machine-learning algorithms as described in further detail below. Training data used by computing device 104 may correlate any input data as described in this disclosure to any output data as described in this disclosure.

With continued reference to FIG. 1, computing device 104 may be configured to generate land classifier 128 using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as $P(A/B)=P(B/A) P(A) \div P(B)$, where $P(AB)$ is the probability of hypothesis A given data B also known as posterior probability; $P(B/A)$ is the probability of data B given that the hypothesis A was true; $P(A)$ is the probability of hypothesis A being true regardless of data also known as prior probability of A; and $P(B)$ is the probability of the data regardless of the hypothesis. A naïve Bayes algorithm may be generated by first transforming training data into a frequency table. Computing device 104 may then calculate a likelihood table by calculating probabilities of different data entries and classification labels. Computing device 104 may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary. With continued reference to FIG. 1, computing device 104 may be configured to generate land classifier 128 using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 1, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute l as derived using a Pythagorean norm: $l=\sqrt{\Sigma_{i=0}^n a_i^2}$, where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values. As a non-limiting example, K-nearest neighbors algorithm may be configured to classify an input vector containing a biological extraction to an output vector containing a land descriptor 116.

With continued reference to FIG. 1, computing device 104 is configured to generate a land machine-learning model 132. A "land machine-learning model," as used in this disclosure, is a machine-learning model that utilizes a biological extraction and a land descriptor 116 as an input and outputs property elements 136. A "machine-learning model," as used in this disclosure, is a process that automatedly uses a body of data known as "training data" and/or a "training set" to generate an algorithm that will be performed by a computing device 104 to produce outputs given data provided as inputs; this is in contrast to a non-machine-learning software program where the commands to be executed are determined in advance by a user and written in a programming language. A land machine-learning model may be used by computing device 104 to output a property element 136 as described below in more detail.

With continued reference to FIG. 1, land machine-learning model 132 may include supervised machine-learning algorithms. Supervised machine learning algorithms, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include elements of physiological data as described above as inputs, property element 136 as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data. Persons skilled in the art, upon reviewing the entirety of this disclosure, will be aware of various possible variations of supervised machine learning algorithms that may be used to determine relation between inputs and outputs. Supervised machine-learning processes may include classification algorithms as defined above. Classification may be performed using, without limitation, linear classifiers such as without limitation logistic regression and/or naive Bayes classifiers, nearest neighbor classifiers including without limitation k-nearest neighbors classifiers, support vector machines, decision trees, boosted trees, random forest classifiers, and/or neural network-based classifiers.

Still referring to FIG. 1, machine learning processes may include unsupervised processes. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

With continued reference to FIG. 1, machine-learning processes as described in this disclosure may be used to generate machine-learning models. A machine-learning model, as used herein, is a mathematical representation of a relationship between inputs and outputs, as generated using any machine-learning process including without limitation any process as described above, and stored in memory; an input is submitted to a machine-learning model once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model may be generated by creating an artificial neural network, such as a convolutional neural network comprising an input layer of nodes, one or more intermediate layers, and an output layer of nodes. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 1, at least a machine-learning process may include a lazy-learning process and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data. Heuristic may include selecting some number of highest-ranking associations and/or training data elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

With continued reference to FIG. 1, at least a machine learning process may include a process classifying and/or scoring options according to any criterion used for and/or referred to in any educational inquiry. For instance, and without limitation, at least a machine-learning process may include a mental health suitability classification process and/or scoring algorithm that scores and/or classifies options according to quality and/or availability of mental health supports and/or protocols, as needed by or necessary given biological extraction 108, and/or according to degree of mental health issues in a student body as relevant to biological extraction 108. As a further example, at least a machine-learning process may include a special needs suitability classification process and/or scoring algorithm that scores and/or classifies options according to quality and/or availability of special needs supports and/or protocols, as needed by or necessary given biological extraction 108. As a further example, at least a machine-learning process may include a disability accommodation suitability classification process and/or scoring algorithm that scores and/or classifies options according to quality and/or availability of disability accommodations such as without limitation learning disability accommodations, as needed by or necessary given biological extraction 108.

Continuing to refer to FIG. 1, machine-learning algorithm may be implemented using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure, Still referring to FIG. 1, machine-learning algorithm may include, without limitation, linear discriminant analysis. Machine-learning algorithm may include quadratic discriminate analysis. Machine-learning algorithm may include kernel ridge regression. Machine-learning algorithm may include support vector machines, including without limitation support vector classification-based regression processes. Machine-learning algorithm may include stochastic gradient descent algorithms, including classification and regression algorithms based on stochastic gradient descent. Machine-learning algorithm may include nearest neighbors algorithms. Machine-learning algorithm may include Gaussian processes such as Gaussian Process Regression. Machine-learning algorithm may include cross-decomposition algorithms, including partial least squares and/or canonical correlation analysis. Machine-learning algorithm may include naïve Bayes methods. Machine-learning algorithm may include algorithms based on decision trees, such as decision tree classification or regression algorithms. Machine-learning algorithm may include ensemble methods such as bagging meta-estimator, forest of randomized tress, AdaBoost, gradient tree boosting, and/or voting classifier methods. Machine-learning algorithm may include neural net algorithms, including convolutional neural net processes.

With continued reference to FIG. 1, models may be generated using alternative or additional artificial intelligence methods, including without limitation by creating an artificial neural network, such as a convolutional neural network comprising an input layer of nodes, one or more intermediate layers, and an output layer of nodes. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. This network may be trained using training data.

With continued reference to FIG. 1, computing device 104 generates an output containing property element 136 utilizing land machine-learning model 132. A "property element," as used in this disclosure, is any numerical, textual, and/or character data indicating a probability of a user safely residing at a property based on a user's biological extraction. A "property," as used in this disclosure, is any land identified within a land descriptor. A property element 136 may indicate a likelihood that a property may contribute to and/or worsen a medical condition and/or diagnosis of a user. For example, a property element 136 may indicate that a house contains very high levels of mold which may be toxic to a user with a biological extraction that indicates the user has allergic asthma. In yet another non-limiting example, a property element 136 may indicate that a house located along a golf course is not toxic for a user who does not have a mutation to methylenetetrahydrofolate reductase (MTHFR) mutation. A property element 136 may indicate a numerical probability as to how safely a user can reside at a property. For example, a property element 136 may be based on a numerical score range, such as from 1-100, where a 1 may indicate a property is definitely not safe for a user to live at a property based on the user's biological extraction, while a 100 may indicate a property is safe for a user to reside based on the user's biological extraction. A property element 136 may indicate if a property contains suitable air quality for a user, if the location of a property will allow for a user to produce sufficient Vitamin D from the amount of sunshine available and the like. A property element 136 may indicate if a property is positioned at an altitude and/or elevation that is compatible with a user's biological extraction. A property element 136 may indicate if a user will have access to fresh water on the user's land or if the water supply may be full of contaminants and may not be compatible for a user's biological extraction.

With continued reference to FIG. 1, computing device 104 is configured to identify an output property factor that indicates a property is not suitable for a user. A property may not be suitable for a user when the property may not be safe for the user to reside or live at the property based on the user's biological extraction. A property may not be safe for a user to live at, when the property may be probabilistically likely to cause the user to develop a new health condition and/or diagnosis, worsen an existing health condition and/or diagnosis, and/or propagate a probability that a user will develop a health condition and/or diagnosis. A property may be safe for a user to live at, when the property may be probabilistically unlikely to cause the user to develop a new health condition and/or diagnosis, worsen an existing health condition and/or diagnosis, and/or propagate a probability that a user will develop a health condition and/or diagnosis. In an embodiment, a particular property element 136 score may indicate if a property may be safe for a user to live at or not. For instance and without limitation, a property element 136 score that contains a numerical score below 75% may be considered unsafe for a user to live at, while a property element 136 score that contains a numerical score at and above 75% may be considered safe for the user to live at. Computing device 104 may locate a property that is suitable for the user if the output property element 136 indicates the property is not suitable for the user. In an embodiment, computing device 104 may locate a second property that is suitable for a user within a certain geographical distance of a first property that is deemed to not be suitable for the user. For instance and without limitation, computing device 104 may determine that a first property located in a neighborhood in Phoenix, Ariz. that contains high levels of solvents and volatile organic compounds (VOCs) after being built on contaminated land may not be suitable for a user with impaired liver function and an inability to detox environmental toxins, while a second property located two miles away in the same neighborhood in Phoenix, Ariz. that does not contain high levels of solvents and VOCs may be suitable for the user. In yet another non-limiting example, computing device 104 may determine that a first property located in a first geographical region is not suitable for a user based on the user's biological extraction, and a second property located in a second geographical region is suitable for the user based on the user's biological extraction. For instance and without limitation, computing device 104 may determine that a first property located in the Northeast where there are many cold, long, dark, and snowy winters may not be suitable for a user with chronic Lyme disease, while a second property located in sunny California along the coast with access to fresh sea air may be suitable for the user with chronic Lyme disease.

With continued reference to FIG. 1, computing device 104 may locate a suitable property for a user utilizing output property element 136 and one or more stored user property preference 140. A "user property preference," as used in this disclosure, is data describing any factor that may influence a user's purchase of a property which may be identified within a land descriptor. Computing device 104 may store one or more user property preference 140 in user database 112. A user property preference 140 may indicate one or more user preferences regarding features in a property that a user has always wanted, such as the ability to watch sunsets from a balcony or the ability to have a picturesque view of snow-capped mountains. A user property preference 140 may indicate a user's preference regarding a neighborhood and/or surrounding area that a user seeks to live at. For example, a user property preference 140 may indicate that a user would like to be able to walk to a coffee shop each morning from the user's property. A user property preference 140 may indicate a user's preference regarding property location and size. For example, a user may prefer a lot that allows for kids to run around in or a lot that has water views. A user property preference 140 may indicate a user's preference in regard to the age of a property such as a user who may prefer an older Victorian style house as compared to a sleek modern house with glass walls. A user property preference 140 may indicate a user's preference in regard to an ideal home style such as if a user prefers a houseboat to a condominium or a town home to a Tudor style house. A user property preference 140 may indicate a user's budget, and how much a user can afford to pay in a mortgage each month. A user property preference 140 may indicate a user's preference as to how long the user plans to live at a property, such as if the user owns multiple properties and will only be living at the property a few weeks each year, or if the user plans to reside at the property full time for the foreseeable future.

With continued reference to FIG. 1, computing device 104 may compare output property element 136 to stored user property preference 140 and locate a property that is suitable for the user based on the output property element 136 and the stored user property preference 140. For instance and without limitation, computing device 104 may determine that an output property element 136 that indicates the property is compatible with a user's biological extraction may not be suitable for the user based on a stored user property preference 140, because the property does not have any water views, and the user has a preference for water views. In yet another non-limiting example, computing device 104 may determine that an output property element 136 that indicates a property is compatible with a user's biological extraction may be suitable for the user when the property contains a large backyard that has space for a built in pool, as requested in a stored user property preference 140. In an embodiment, one or more details regarding a property may be stored within property database 144. Property database 144 may be implemented as any data structure suitable for use as user database 112 as described above.

With continued reference to FIG. 1, computing device 104 may be configured to determine that output property element 136 indicate unsuitability of a property for a user. Computing device 104 may determine unsuitability of a property, when the property may not be safe for the user to reside or live at the property based on the user's biological extraction. Computing device 104 may recommend a neutralizer element 148 to the user to make the property suitable for the user based on the user's biological extraction. A "neutralizer element," as used in this disclosure, identifies any action that can be taken by a user to improve the habitability of a property based on the user's biological extraction. A neutralizer element 148 may identify an ameliorative treatment that may correct and/or remedy an unsuitable condition at a property. For instance and without limitation, an ameliorative treatment may identify a glutathione suppository that a user can utilize for six weeks to detoxify from heavy metals before moving into a property that is considered unsuitable for the user because the property contains water contaminated with heavy metals and may further precipitate the user's toxicity load. In yet another non-limiting example, a neutralizer element 148 may identify an ameliorative treatment such as a methylated b-vitamin supplement a user can consume to correct a user's b-vitamin deficiency caused by a MTHFR mutation that causes the user to be prone to toxicity, before considering living at a property that was contaminated with cadmium. A neutralizer element 148 may identify a solution that may be applied to a property in order to correct and make the property suitable for the user. For instance and without limitation, a neutralizer element 148 may identify a filtration system that may be installed at a property to remove heavy metals and contaminants from water. In yet another non-limiting example, a neutralizer element 148 may identify a solution that recommends removing a smart house wiring system to eliminate toxicity from strong magnetic fields and aluminum wiring that may be present in the smart house wiring system. In yet another non-limiting example, a neutralizer element 148 may identify organic lawn products that can be applied to a law to eliminate the need to apply toxic lawn products that may cause teratogenicity in a user who is pregnant. Computing device 104 may indicate a period when a neutralizer element 148 will make a property suitable for a user. For example, computing device 104 may identify a neutralizer element 148 that recommends using organic fertilizer for all outdoor plants for a minimum of six weeks before the property will be suitable for a user with a biological extraction that shows an apolipoprotein E4 gene, thereby making the user susceptible to toxicity from inorganic fertilizers. In yet another non-limiting example, computing device 104 may identify a neutralizer element 148 that recommends shielding the exterior of a house with T98 shielding paint to reduce exposure to magnetic fields produced by power lines located adjacent to a property, with a minimum recommendation of waiting four weeks after application of the T98 shielding paint before the property will become suitable for a user.

With continued reference to FIG. 1, computing device 104 may be configured to update land machine-learning model 132. Computing device 104 may utilize a user biological extraction and an output property element 136 to update land machine-learning model 132. This may allow for land machine-learning model 132 to continuously be updated and to further refine input and output pairs.

Figure 2:
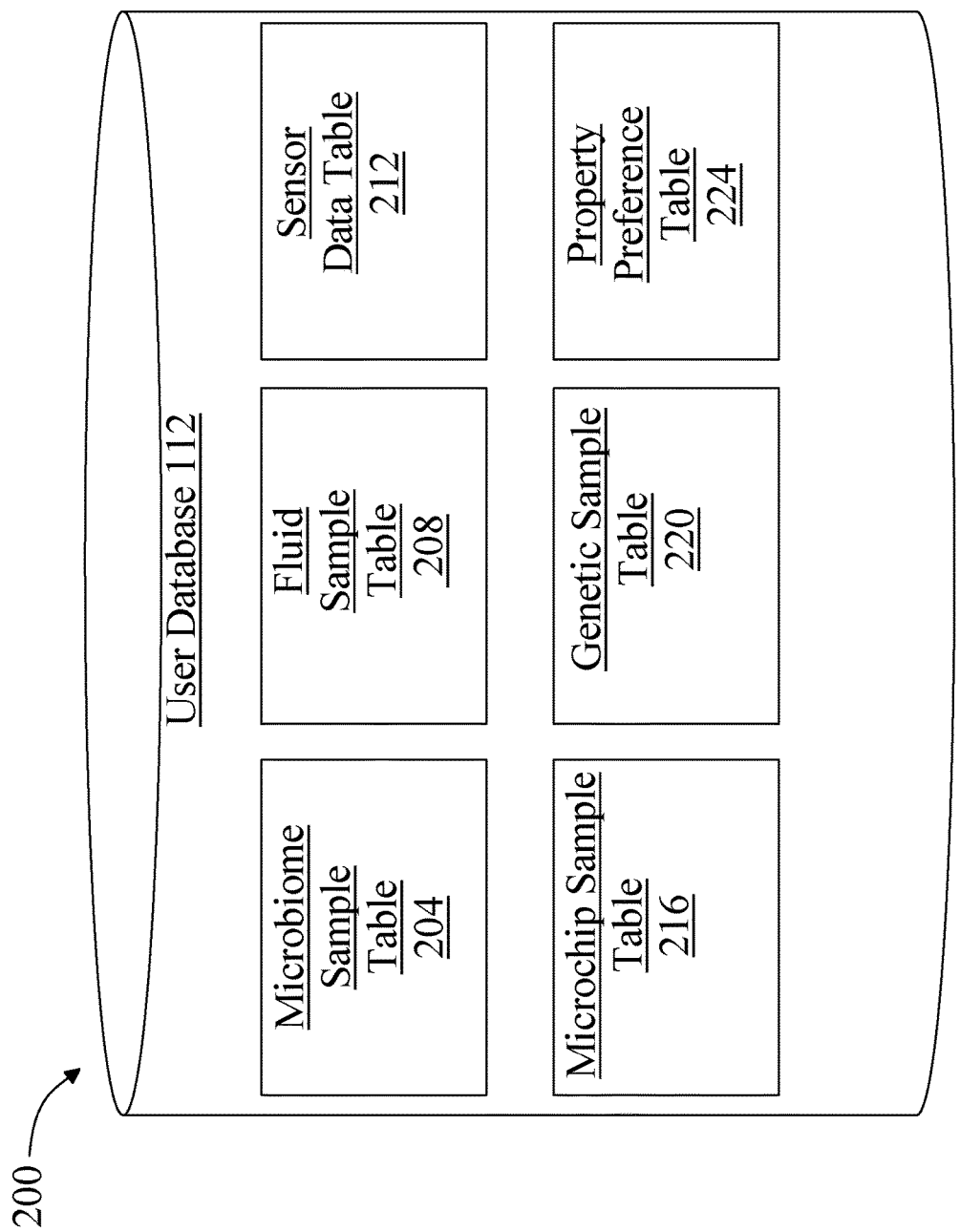
FIG. 2 is a block diagram illustrating an exemplary embodiment of a user database.

Referring now to FIG. 2, an exemplary embodiment of user database 112 is illustrated. User database 112 may be implemented as any data structure as described above in more detail. One or more tables contained within user database 112 may include microbiome sample table 204; microbiome sample table 204 may include one or more biological extraction relating to the microbiome. For instance and without limitation, microbiome sample table 204 may include a physically extracted sample such as a stool sample analyzed for the presence of pathogenic species such as parasites and anaerobes. One or more tables contained within user database 112 may include fluid sample table 208; fluid sample table 208 may include one or more biological extraction containing fluid samples. For instance and without limitation, fluid sample table 208 may include a urine sample analyzed for the presence or absence of glucose. One or more tables contained within user database 112 may include sensor data table 212; sensor data table 212 may include one or more biological extraction containing sensor measurements. For instance and without limitation, sensor data table 212 may include heart rate, blood pressure, and glucose readings. One or more tables contained within user database 112 may include microchip sample table 216; microchip sample table 216 may include one or more biological extraction obtained from a microchip. For instance and without limitation, microchip sample table 216 may include an intracellular nutrient level obtained from a microchip embedded under a user's skin. One or more tables contained within user database 112 may include genetic sample table 220; genetic sample table 220 may include one or more biological extraction containing genetic samples. For instance and without limitation, genetic sample table 220 may include a blood test analyzed for the apolipoprotein E4 variant (APOE4). One or more tables contained within user database 112 may include property preference table 224; property preference table 224 may include one or more user property preference 140. For instance and without limitation, property preference table 224 may include a user preference to have a property that is of a Tudor style architecture and has an indoor swimming pool.

Figure 3:
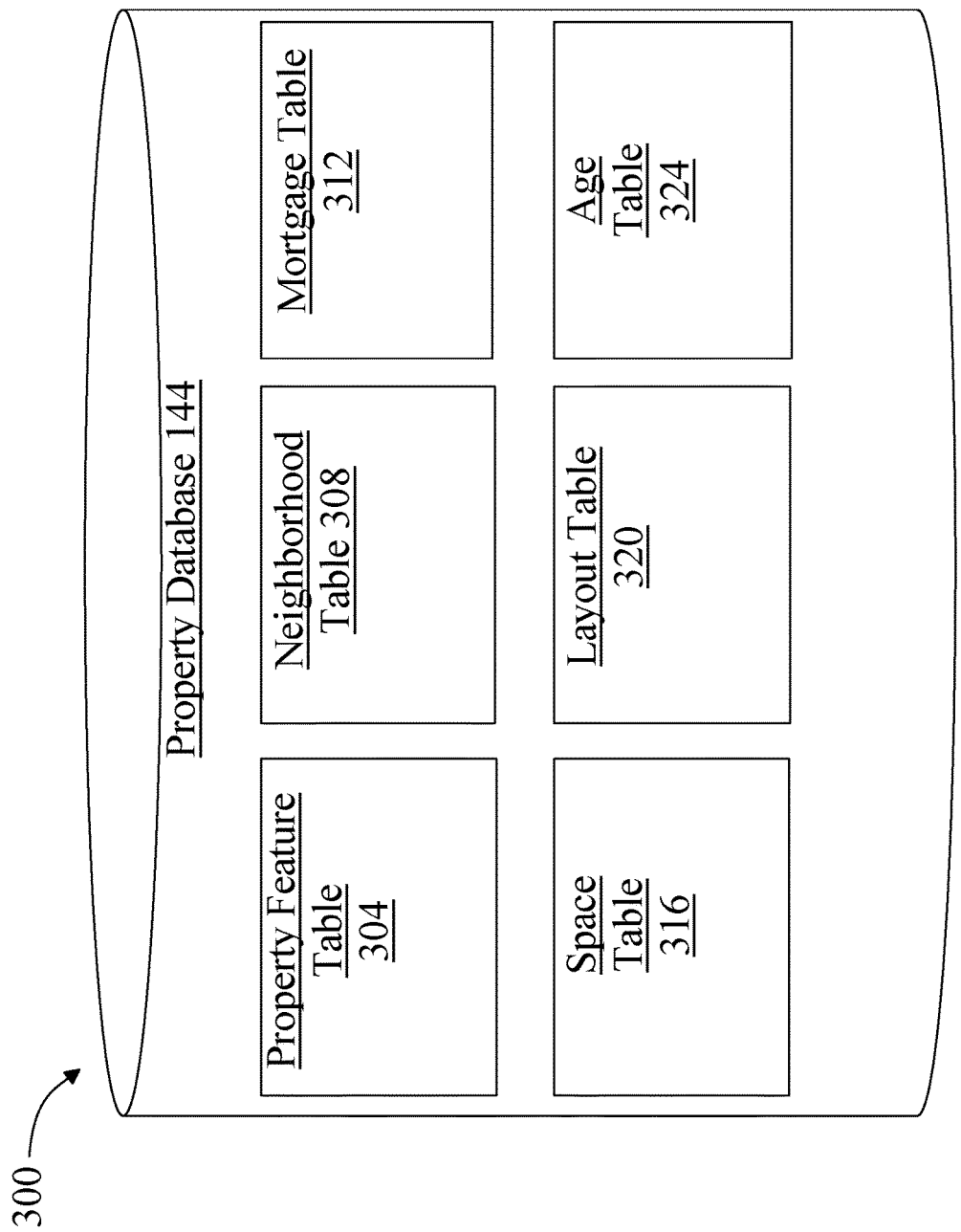
FIG. 3 is a block diagram illustrating an exemplary embodiment of a property database.

Referring now to FIG. 3, an exemplary embodiment of property database 144 is illustrated. Property database 144 may be implemented as any data structure as described above. One or more tables contained within property database 144 may include property feature table 304; property feature table 304 may include one or more property features contained within a property. For instance and without limitation, property feature table 304 may describe a lake view that a property has or a property that contains a patio that has mountain views. One or more tables contained within property database 144 may include neighborhood table 308; neighborhood table 308 may include one or more neighborhood features of a property. For instance and without limitation, neighborhood table 308 may describe a property that does not have noisy neighbors or a property that is within walking distance of local restaurants. One or more tables contained within property database 144 may include mortgage table 312; mortgage table 312 may include one or more projected mortgage rates for a property. For instance and without limitation, mortgage table 312 may describe a property that has an estimated $1500/month mortgage payment. One or more tables contained within property database 144 may include space table 316; space table 316 may include a description of space contained within a property. For instance and without limitation, space table 316 may indicate how many rooms a property has and how many square feet the property is. One or more tables contained within property database 144 may include layout table 320; layout table 320 may describe the layout of a property. For instance and without limitation, layout table 320 may describe the living space of a property. One or more tables contained within property database 144 may include age table 324; age table 324 may include one or more factors indicating how old a property may be. For example, age table 324 may indicate that a property was built one hundred and fifty years ago.

Figure 4:
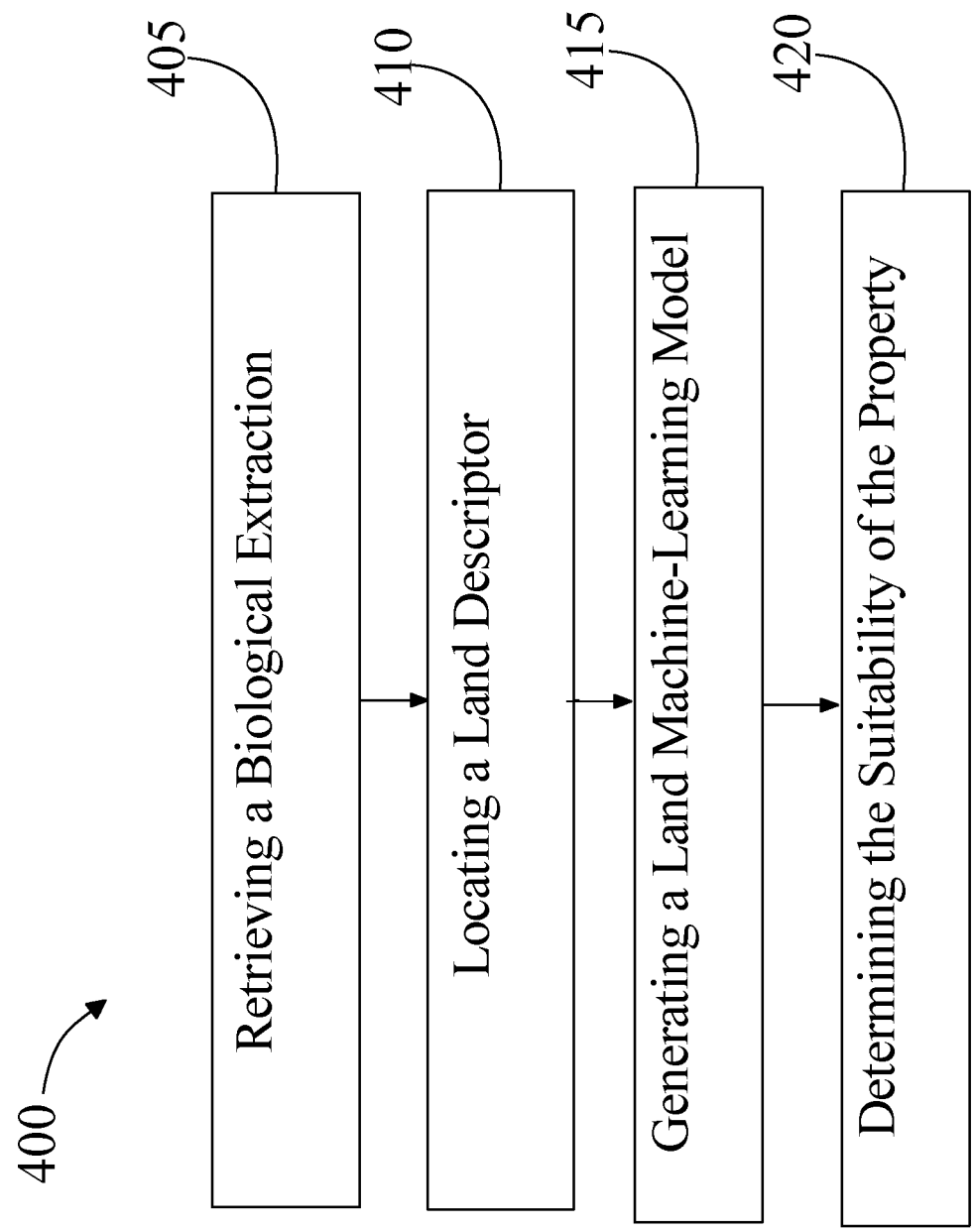
FIG. 4 is a process flow diagram illustrating an exemplary embodiment of an artificial intelligence method of generating land responses from biological extractions.

Referring now to FIG. 4, an exemplary embodiment 400 of an artificial intelligence method of generating land responses from biological extractions is illustrated. At step 405, a computing device retrieves a biological extraction pertaining to a user. A biological extraction includes any of the biological extractions as described above in reference to FIG. 1. A biological extraction contains at least an element of user physiological data. For instance and without limitation, a biological extraction may include a saliva sample analyzed for hormone levels including progesterone, estriol, estrone, estradiol, testosterone, and cortisol. In yet another non-limiting example, a biological extraction may include a stool test analyzed for one or more microbe levels. Computing device 104 may retrieve one or more biological extractions from user database 112.

With continued reference to FIG. 4, at step 410, a computing device 104 locates a land descriptor 116, wherein the land descriptor 116 identifies a property. A land descriptor 116, includes any of the land descriptors as described above in reference to FIG. 1. A land descriptor 116 may describe a structure, including any residential structure, any commercial structure, any industrial structure, and/or vacant land. Computing device 104 may located a land descriptor 116 based on a user geolocation 120. For instance and without limitation, a remote device 124 such as a user's cellphone may transmit to computing device 104 an element of user data containing a user's geolocation, describing the latitude and longitude where the user is presently located. Computing device 104 may locate a land descriptor 116 identifying a property located within the user's geolocation. For instance and without limitation, a user's geolocation data showing the user's latitude and longitude may indicate that the user is presently located in San Diego, Calif. In such an instance, computing device 104 may locate a land descriptor 116 within San Diego, Calif.

With continued reference to FIG. 4, a land descriptor 116 may be located based on one or more user responses contained within a user questionnaire response that may contain a user's preferences describing an ideal land descriptor 116. For example, a user's questionnaire response may indicate that the user seeks to find a ranch style house that contains four bedrooms. In such an instance, computing device 104 may locate a land descriptor 116 that matches the user's preferences contained within the user's questionnaire. In an embodiment, a land descriptor 116 may contain a specific address of a particular structure. For example, a land descriptor 116 may contain a specific address that reads as "3 Main Street, Louisville Ky." In an embodiment, a land descriptor 116 may describe a particular geographical location. For example, a land descriptor 116 may describe a geographical location such as the Southeast including Alabama, Florida, Georgia, Kentucky, Maryland, Mississippi, North Carolina, and South Carolina. In yet another non-limiting example, a land descriptor 116 may describe a geographical location such as the west coast of the United States, or the Northwest region of Connecticut. In an embodiment, a land descriptor 116 may describe a county such as Orange county in California.

With continued reference to FIG. 4, computing device 104 may locate a land descriptor 116 utilizing land classifier 128. Land classifier 128 utilizes one or more classification algorithms, in combination with training data to utilize a biological extraction as an input and output a land descriptor 116. Classification algorithm includes any of the classification algorithms as described above in reference to FIG. 1.

With continued reference to FIG. 4, at step 415, a computing device 104 generates a land machine-learning model 132. Land machine-learning model 132 includes any of the machine-learning models as described above in reference to FIG. 1. Land machine-learning model 132 utilizes a biological extraction and a land descriptor 116 as an input, and outputs property element 136. A property element 136 includes any numerical, textual, and/or character data, indicating a probability of a user safely residing at a property based on a user's biological extraction. A property element 136 may indicate a likelihood that a property may contribute to and/or worsen a medical condition and/or diagnosis of a user. For instance and without limitation, a property element 136 may indicate that a property identified within a land descriptor 116 has an 80% probability of being compatible for a user with a biological extraction that shows the user has elevated blood triglyceride levels. In yet another non-limiting example, a property element 136 may indicate that a property identified within a land descriptor 116 has a 27% probability of being compatible for a user with a biological extraction that reflects high blood mercury levels.

With continued reference to FIG. 4, at step 420, a computing device 104 determines the suitability of a property utilizing output property element 136. A property element 136 is any numerical, textual, and/or character data indicating a probability of a user safely residing at a property based on a user's biological extraction. A property element 136 may indicate a likelihood that a property may contribute to and/or worsen a medical condition and/or diagnosis of a user. A property may not be suitable for a user when the property may not be safe for the user to reside or live at the property based on the user's biological extraction as described above in more detail. A property may be suitable for a user when the property may be safe for the user to reside or live at the property based on the user's biological extraction as described above in more detail. For instance and without limitation, a property that contains high levels of phthalates in vinyl flooring may not be suitable for a user with impaired metabolic pathways as demonstrated by elevated liver enzymes. In yet another non-limiting example, a property that contains water contaminated with copper may be suitable for a user with a genetic sequence showing that the user is an ultra-rapid metabolizer. Computing device 104 may identify an output property element 136 that indicates a property is not suitable for a user. For example, computing device 104 may determine that a property that is geographically positioned to receive direct sunlight exposure, may not be compatible for a user with a biological extraction showing the user has an extreme sensitivity to ultraviolet rays from sunlight. In such an instance, computing device 104 locates a property that is suitable for the user. For example, computing device 104 may locate a property that has very little direct sunlight exposure. In an embodiment, computing device 104 may locate a property contained within a certain geographical region and/or location identified within a land descriptor 116. For instance and without limitation, computing device 104 may identify a first property located in Austin, Tex. that is not suitable for a user, whereby computing device 104 may identify a second property located in Austin, Tex. that is suitable for the user. In yet another non-limiting example, computing device 104 may identify a first property located in the Midwest that is not suitable for a user, whereby computing device 104 may identify a second property located in the Midwest that is suitable for the user. Computing device 104 may identify a property element 136 that may indicate if a property identified within a land descriptor contains air quality that is compatible with a user's biological extraction. A property element 136 may indicate if a property is positioned at a compatible elevation and/or altitude that is compatible with a user's biological extraction. A property element 136 may indicate if a property will allow a user to produce sufficient Vitamin D from the amount of sunshine that is available based on the geographical location of a property. A property element 136 may indicate if a property has access to drinking water that is compatible with a user's biological extraction. A property element 136 may indicate if a property has sufficient land to grow food that is compatible with a user's biological extraction.

With continued reference to FIG. 4, computing device 104 may identify a neutralizer element 148 to transform a property from being considered an unsuitable property to a suitable property. A neutralizer element 148 identifies any action that can be taken by a user to improve the habitability of a property based on the user's biological extraction. A neutralizer element 148 may include an ameliorative neutralizer element 148 that identifies a particular remedy that may correct and/or remedy an unsuitable condition at a property. For instance and without limitation, a neutralizer element 148 may include a supplement that a user may take to correct a nutrient deficiency. In yet another non-limiting example, a neutralizer element 148 may include a neutralizer element 148 that may be applied to a property to make a property suitable for a user. For instance and without limitation, a neutralizer element 148 may include a plant that may be placed inside a property to detoxify air inside the property. In yet another non-limiting example, a neutralizer element 148 may include removal of party of a property, such as the removal of lead based paint and the application of non-toxic paint. In yet another non-limiting example, a neutralizer element 148 may include supplementation with additional minerals that may not be present in drinking water available at a property. Computing device 104 may indicate a period when a neutralizer element 148 will make a property suitable for a user. For example, computing device 104 may indicate that a user may need to supplement with chlorella to detoxify the user's body from excess heavy metals for a minimum of twelve weeks before the property will be suitable for the user to live in. In yet another non-limiting example, computing device 104 may indicate that a user may need to place specific peace lily plants in different rooms of a property to detoxify the air for a minimum of three days before the property will become suitable for the user to live at.

With continued reference to FIG. 4, computing device 104 updates land machine-learning model 132 utilizing output property element 136. Computing device 104 may utilize an output property element 136 to update subsequence land machine-learning model 132. In an embodiment, computing device 104 may utilize an input biological extraction and an output property element 136 to update land machine-learning model 132. This may include incorporating an input biological extraction and/or an output property element 136 into subsequent training sets and/or land machine-learning model 132. Computing device 104 may update land classifier 128 to utilize input biological extractions and output land descriptor 116 to update land classifier 128.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 5:
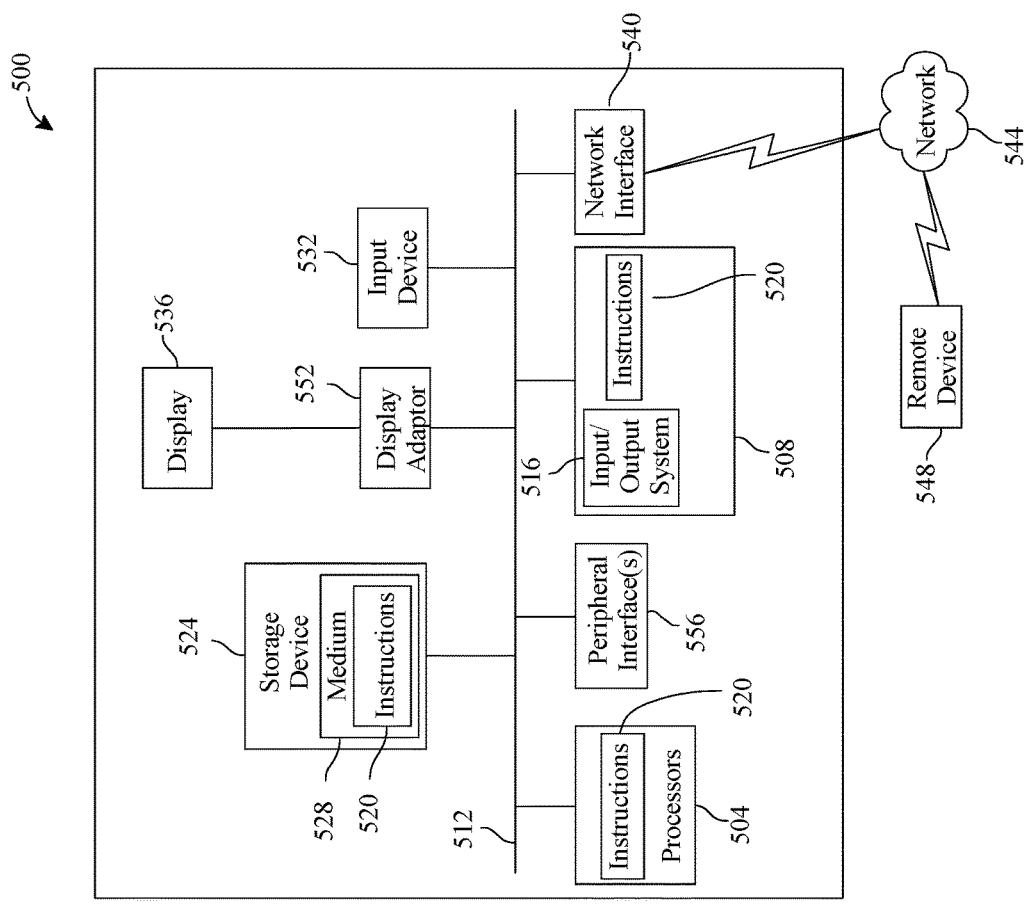
FIG. 5 is a block diagram of a computing system that can be used to implement any one or more of the methodologies disclosed herein and any one or more portions thereof.

FIG. 5 shows a diagrammatic representation of one embodiment of a computing device in the exemplary form of a computer system 500 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 500 includes a processor 504 and a memory 508 that communicate with each other, and with other components, via a bus 512. Bus 512 may include any of several types of bus structures including, but not limited to, a memory bus, a memory controller, a peripheral bus, a local bus, and any combinations thereof, using any of a variety of bus architectures.

Memory 508 may include various components (e.g., machine-readable media) including, but not limited to, a random access memory component, a read only component, and any combinations thereof. In one example, a basic input/output system 516 (BIOS), including basic routines that help to transfer information between elements within computer system 500, such as during start-up, may be stored in memory 508. Memory 508 may also include (e.g., stored on one or more machine-readable media) instructions (e.g., software) 520 embodying any one or more of the aspects and/or methodologies of the present disclosure. In another example, memory 508 may further include any number of program modules including, but not limited to, an operating system, one or more application programs, other program modules, program data, and any combinations thereof.

Computer system 500 may also include a storage device 524. Examples of a storage device (e.g., storage device 524) include, but are not limited to, a hard disk drive, a magnetic disk drive, an optical disc drive in combination with an optical medium, a solid-state memory device, and any combinations thereof. Storage device 524 may be connected to bus 512 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 524 (or one or more components thereof) may be removably interfaced with computer system 500 (e.g., via an external port connector (not shown)). Particularly, storage device 524 and an associated machine-readable medium 528 may provide nonvolatile and/or volatile storage of machine-readable instructions, data structures, program modules, and/or other data for computer system 500. In one example, software 520 may reside, completely or partially, within machine-readable medium 528. In another example, software 520 may reside, completely or partially, within processor 504.

Computer system 500 may also include an input device 532. In one example, a user of computer system 500 may enter commands and/or other information into computer system 500 via input device 532. Examples of an input device 532 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 532 may be interfaced to bus 512 via any of a variety of interfaces (not shown) including, but not limited to, a serial interface, a parallel interface, a game port, a USB interface, a FIREWIRE interface, a direct interface to bus 512, and any combinations thereof. Input device 532 may include a touch screen interface that may be a part of or separate from display 536, discussed further below. Input device 532 may be utilized as a user selection device for selecting one or more graphical representations in a graphical interface as described above.

A user may also input commands and/or other information to computer system 500 via storage device 524 (e.g., a removable disk drive, a flash drive, etc.) and/or network interface device 540. A network interface device, such as network interface device 540, may be utilized for connecting computer system 500 to one or more of a variety of networks, such as network 544, and one or more remote devices 548 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 544, may employ a wired and/or a wireless mode of communication. In general, any network topology may be used. Information (e.g., data, software 520, etc.) may be communicated to and/or from computer system 500 via network interface device 540.

Computer system 500 may further include a video display adapter 552 for communicating a displayable image to a display device, such as display device 536. Examples of a display device include, but are not limited to, a liquid crystal display (LCD), a cathode ray tube (CRT), a plasma display, a light emitting diode (LED) display, and any combinations thereof. Display adapter 552 and display device 536 may be utilized in combination with processor 504 to provide graphical representations of aspects of the present disclosure. In addition to a display device, computer system 500 may include one or more other peripheral output devices including, but not limited to, an audio speaker, a printer, and any combinations thereof. Such peripheral output devices may be connected to bus 512 via a peripheral interface 556. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

The invention claimed is:

1. An artificial intelligence system for generating land responses from biological extractions, the system comprising a computing device, the computing device designed and configured to:
retrieve a biological extraction pertaining to a user, wherein the biological extraction contains at least an element of physiological data;
locate a land descriptor wherein the land descriptor identifies a property;
generate a land machine-learning model, wherein generating the land machine-learning model comprises training the land machine-learning model with training data correlating biological extractions to property elements of a property, wherein the land machine-learning model receives the biological extraction and the land descriptor as an input and outputs property elements;
determine suitability of the property utilizing the output property elements;
determine that the output property elements indicate that the property is unsuitable for the user;
recommend a neutralizer element to make the property suitable for the user based on the user's biological extraction;
indicate a period when the neutralizer element will make the property suitable for the user; and
update the land machine-learning model by training the land machine-learning model with the biological extraction as an input and the suitable property as an output.

2. The system of claim 1, wherein the land descriptor is located as a function of a user geolocation.

3. The system of claim 1, wherein the land descriptor is located as a function of a user questionnaire response wherein the user questionnaire response contains user preferences relating to an ideal land descriptor.

4. The system of claim 1, wherein the land descriptor contains an inquiry describing a specified address.

5. The system of claim 1, wherein the land descriptor contains an inquiry describing a geographical location.

6. The system of claim 1, wherein the computing device is further configured to locate the land descriptor using a land classifier that utilizes the biological extraction as an input and outputs a land descriptor.

7. The system of claim 1, wherein the computing device is further configured to:
identify an output property element that indicates the property is not suitable for the user; and
locate a property that is suitable for the user.

8. The system of claim 1, wherein the computing device is further configured to:
compare the output property elements to stored user property preferences; and
locate a property that is suitable for the user based on the output property elements and the stored user property preferences.

9. The system of claim 1, wherein the computing device is further configured to update the land machine-learning model utilizing the determined suitability of the property.

10. An artificial intelligence method of generating land responses from biological extractions, the method comprising:
retrieving, by a computing device, a biological extraction pertaining to a user, wherein the biological extraction contains at least an element of physiological data;
locating, by the computing device, a land descriptor wherein the land descriptor identifies a property;
generating, by the computing device, a land machine-learning model, wherein the land machine-learning model utilizes the biological extraction and the land descriptor as an input and outputs property elements; and
determining, by the computing device, the suitability of the property utilizing the output property elements;
determining the output property elements indicate the unsuitability of the property for the user;
recommending a neutralizer element to make the property suitable for the user based on the user's biological extraction; and
indicating a period when the neutralizer element will make the property suitable for the user.

11. The method of claim 10, wherein locating the land descriptor further comprises locating the land descriptor as a function of a user geolocation.

12. The method of claim 10, wherein locating the land descriptor further comprises locating the land descriptor utilizing a user questionnaire response wherein the user questionnaire response contains user preferences in response to an ideal land descriptor.

13. The method of claim 10, wherein the land descriptor further comprises an inquiry describing a specified address.

14. The method of claim 10, wherein the land descriptor further comprises an inquiry describing a geographical location.

15. The method of claim 10, wherein locating the land descriptor further comprises generating a land classifier that utilizes the biological extraction as an input and outputs a land descriptor.

16. The method of claim 10, wherein determining the suitability of the property further comprises:
identifying an output property element that indicates the property is not suitable for the user; and
locating a property that is suitable for the user.

17. The method of claim 10, wherein determining the suitability of the property further comprises:
comparing the output property elements to stored user property preferences; and
locating a property that is suitable for the user based on the output property elements and the stored user property preferences.

18. The method of claim 10 further comprising updating the land machine-learning model utilizing the determined suitability of the property.

* * * * *